United States Patent
Jewell et al.

(10) Patent No.: US 10,071,145 B2
(45) Date of Patent: *Sep. 11, 2018

(54) LOCAL ENGINEERING OF THE LYMPH NODE ENVIRONMENT TO PROMOTE IMMUNE TOLERANCE

(71) Applicant: University of Maryland, College Park, College Park, MD (US)

(72) Inventors: Christopher M. Jewell, Silver Spring, MD (US); James I. Andorko, Delran, NJ (US); Lisa H. Tostanoski, Washington, DC (US)

(73) Assignee: UNIVERSITY OF MARYLAND, COLLEGE PARK, College Park, MD (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/449,327

(22) Filed: Mar. 3, 2017

(65) Prior Publication Data
US 2017/0173129 A1    Jun. 22, 2017

Related U.S. Application Data

(63) Continuation of application No. 14/751,772, filed on Jun. 26, 2015, now Pat. No. 9,610,349.

(60) Provisional application No. 62/017,721, filed on Jun. 26, 2014.

(51) Int. Cl.
*A61K 39/00* (2006.01)
*A61K 45/06* (2006.01)

(52) U.S. Cl.
CPC .......... *A61K 39/0008* (2013.01); *A61K 45/06* (2013.01); *A61K 2039/54* (2013.01); *A61K 2039/55511* (2013.01); *A61K 2039/55555* (2013.01); *A61K 2039/577* (2013.01)

(58) Field of Classification Search
None
See application file for complete search history.

(56) References Cited

U.S. PATENT DOCUMENTS

2013/0287729 A1    10/2013    Keselowsky et al.

OTHER PUBLICATIONS

Jewell, C.M., et al., In situ engineering of the lymph node microenvironment via intranodal injection of adjuvant-releasing polymer particles, PNAS, Sep. 20, 2011, vol. 108, No. 38, pp. 15745-15750.

Bar-Or, A., et al., Induction of Antigen-Specific Tolerance in Multiple Sclerosis After Immunization with DNA Encoding Myelin Basic Protein in a Randomized, Placebo-Controlled Phase 1/2 Trial, Arch Neural., 2007, vol. 64, No. 10, pp. 1407-1415.

Lutterotti, A., et al., Antigen-Specific Tolerance by Autologous Myelin Peptide-Coupled Cells: A Phase 1 Trial in Multiple Sclerosis, Sci. Transl. Med., Jun. 5, 2013, vol. 5, No. 188, pp. 188ra75 (11 pages).

Senti, G., et al., Intralymphatic immunotherapy, Cum Opin. Allergy. Clin. Immunol., 2009, vol. 9, No. 6, pp. 537-543.

Johansen, P., et al., Direct intralymphatic injection of peptide vaccines enhances immunogenicity, Eur. J. Immunol., 2005, vol. 35, No. 2, pp. 568-574.

Jhunjhunwala, S., et al., Controlled release formulations of IL-2, TGF-beta1 and rapamycin for the induction of regulatory T cells, J. Control. Release, 2012, vol. 159, No. 1, pp. 78-84.

Yeste, A., et al., Nanoparticle-mediated codelivery of myelin antigen and a tolerogenic small molecule suppresses experimental autoimmune encephalomyelitis, Proc. Natl. Acad. Sci. U S A, 2012, vol. 109, No. 28, pp. 11270-11275.

Haddadi, A., et al., Delivery of rapamycin by PLGA nanoparticles enhances its suppressive activity on dendritic cells, J. Biomed. Mater. Res. A, 2008, vol. 84, No. 4, pp. 885-898.

Jhunjhunwala, S., et al., Delivery of rapamycin to dendritic cells using degradable microparticles, J. Control. Release, 2009, vol. 133, No. 3, pp. 191-197.

T Hart, B., et al., Modelling of multiple sclerosis: lessons learned in a non-human primate, The Lancet Neurology, Oct. 2004, vol. 3, No. 10, pp. 588-597.

Werkerle, H., et al., Animal modles of multiple sclerosis, Drug Discovery Today: Disease Models, 2006, vol. 3, No. 4, pp. 359-367.

Ransohoff, R.M., Animal Models of multiple sclerosis: the good, the bad and the bottom line, Nature Neuroscience, Aug. 2012, vol. 15, No. 8, pp. 1074-1077.

Behan, P.O., et al., The sad plight of multiple sclerosis research (low on fact, high on fiction): critical data to support it being a neurocristopathy, Inflammopharmacology, 2010, vol. 18, pp. 265-290.

Whitacre, C.C., et al., Treatment of Autoimmune Disease by Oral Tolerance to Autoantigens, Clinical Immunology and Immunopathology, Sep. 1996, vol. 80, No. 3, pp. S31-S39.

*Primary Examiner* — John D Ulm
(74) *Attorney, Agent, or Firm* — Hodgson Russ LLP

(57) ABSTRACT

A method of inducing specific immune tolerance to myelin in an individual is provided. The method includes introducing directly into a lymph node of the individual an effective amount of a composition that contains a myelin antigen, a biodegradable material and at least one tolerogenic agent. The method is suitable for reducing the severity of symptoms of multiple sclerosis in individuals who suffer from primary-progressive multiple sclerosis (PPMS), and can halt or even reverse PPMS progression.

6 Claims, 15 Drawing Sheets
(13 of 15 Drawing Sheet(s) Filed in Color)

Figure 2
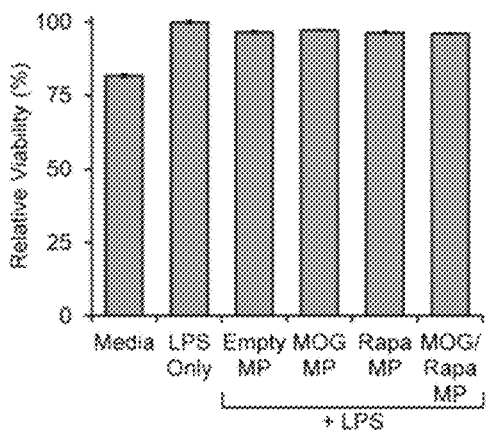
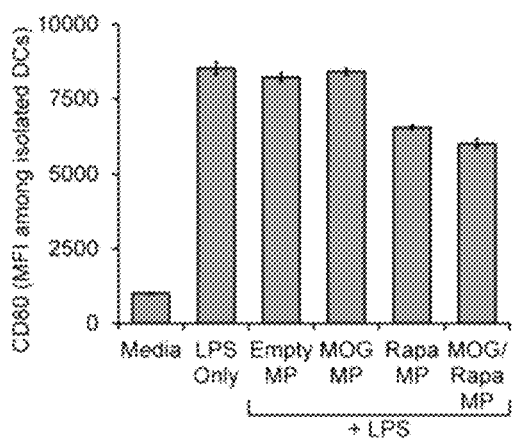
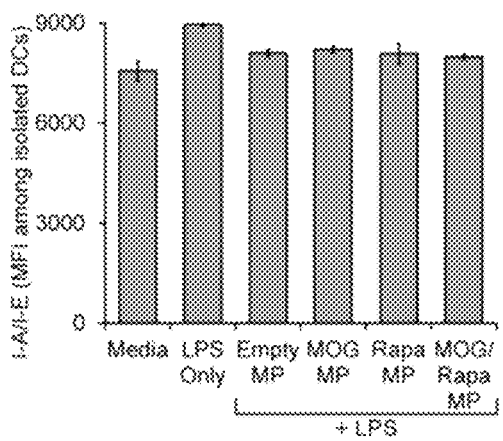

Figure 3
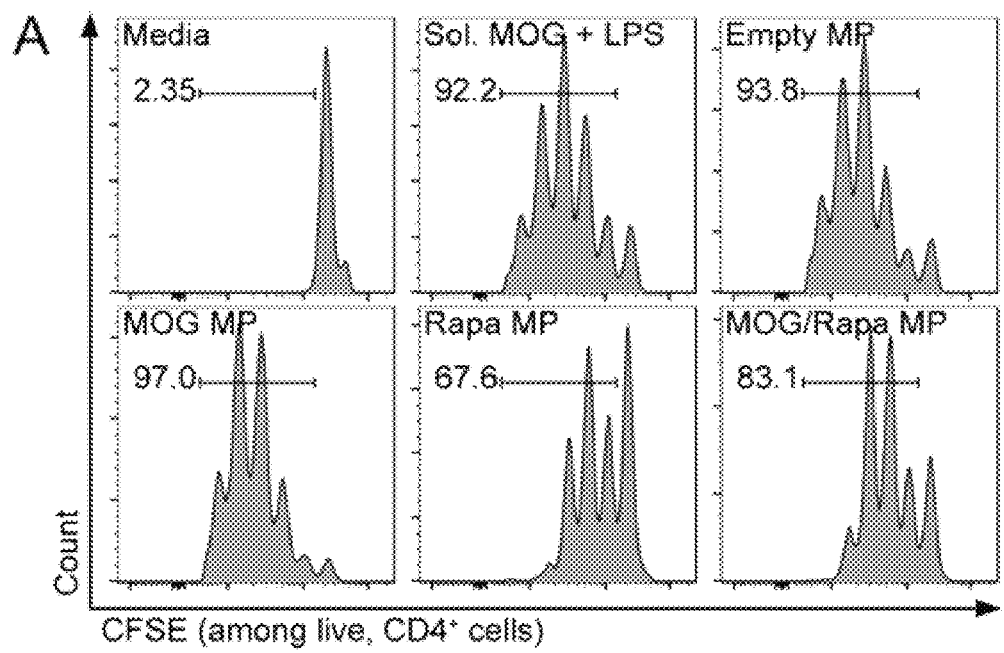
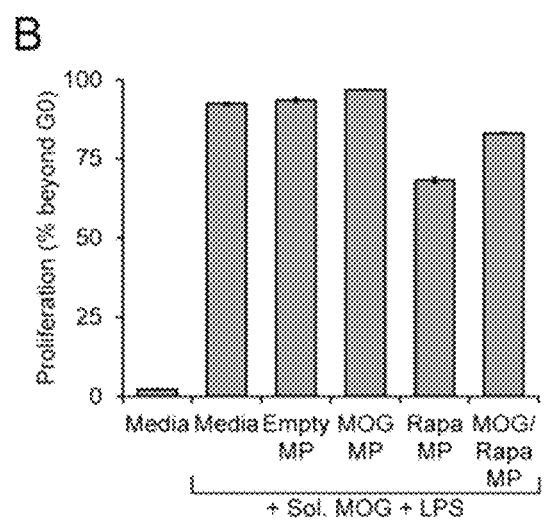

Figure 12
Empty MP Treated
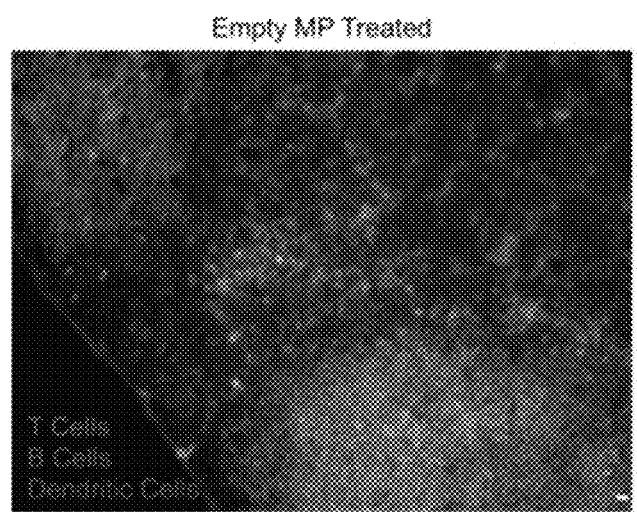
MOG/Rapa MP Treated "Responder"
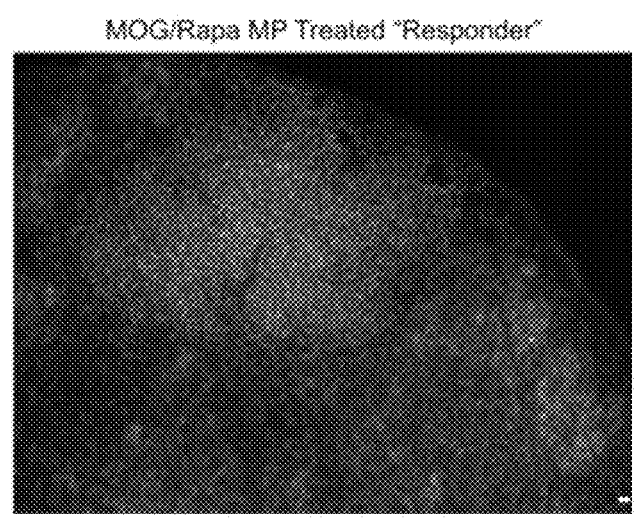

LOCAL ENGINEERING OF THE LYMPH NODE ENVIRONMENT TO PROMOTE IMMUNE TOLERANCE

CROSS-REFERENCE TO RELATED APPLICATIONS

This application is a continuation of U.S. patent application Ser. No. 14/751,772, filed Jun. 26, 2015, which claims priority to U.S. Provisional Patent Application No. 62/017,721, filed Jun. 26, 2014, the disclosures of each of which are incorporated herein by reference.

BACKGROUND OF THE DISCLOSURE

Therapeutic vaccination is an intriguing approach for combating autoimmune disease because this strategy provides an opportunity for highly specific treatment. Unfortunately, these vaccines have had mixed results in clinical trials as directing the nature of immune response in a particular population (e.g., regulatory T cells, TREGS) is challenging. One way to address this limitation is to design vaccines incorporating immunomodulatory small molecules—drugs capable of biasing immune response. However, the rapid in vivo clearance of these hydrophobic drugs and an inability to locally target particular immune populations creates a severe functional limitation. Controlled, local delivery of vaccines (e.g., antigens, adjuvants) and immunomodulators could allow for therapies that induce immune responses tuned for particular diseases. However, there remains an ongoing and unmet need for improved approaches for therapeutic vaccination, particularly in the autoimmune field. The present disclosure addresses these needs.

SUMMARY OF THE DISCLOSURE

The present disclosure relates to a method of inducing specific immune tolerance to myelin in an individual in need thereof, such as individual who has been diagnosed with or is suspected of having multiple sclerosis (MS). The method generally comprises introducing directly into a lymph node of the individual an effective amount of a composition comprising a myelin antigen, a biodegradable material such as a polymer, and at least one tolerogenic agent, such that tolerance to the myelin antigen in the individual is induced. In embodiments, the composition does not comprise any surface ligand that specifically targets the composition to any cell or tissue. The compositions include cell-free compositions. The method is unexpectedly suitable for reducing the severity of MS symptoms in individuals with primary-progressive multiple sclerosis (PPMS). Thus, in certain embodiments, by administering a composition of the disclosure to the individual, the severity of at least one symptom of multiple sclerosis in the individual is reduced. In certain embodiments, a reduction in the severity of MS symptoms in PPMS patients comprises a slowing of the progression of PPMS, a cessation of the progression of the PPMS, or elimination of at least one symptom of the PPMS. In embodiments, such results are achieved by introducing the composition directly into the lymph node of the individual not more than one time. This approach can also produce a systemic reduction of inflammation in the individual. These benefits are demonstrated using a clinically relevant model of PPMS. In particular, the Experimental Autoimmune Encephalomyelitis (EAE) mouse model is used to demonstrate that a single intra-lymph nodal dose of a representative myelin antigen (MOG) and a representative immunomodulatory compound (rapamycin) in a representative biodegradable polymer (poly(lactide-co-galactide) (PLGA)), was able to prevent the onset of symptoms of paralysis in 50% of treated mice. Further, treated mice that developed disease symptoms had delayed disease onset. Those mice also developed less severe symptoms compared to untreated controls. Accordingly, the present disclosure provides a therapeutically feasible approach for not only reducing, but stopping and even reversing progression of symptoms of MS, including PPMS.

BRIEF DESCRIPTION OF THE FIGURES

The patent or application file contains at least one drawing executed in color. Copies of this patent or patent application publication with color drawing(s) will be provided by the Office upon request and payment of the necessary fee.

FIG. 2. CD11c$^+$ splenic dendritic cells were treated with soluble LPS and microparticle (MP) formulations encapsulating indicated cargos. A) Minimal impact on cell viability was observed, irrespective of cargo. B) MPs encapsulating Rapa or co-loaded with MOG and Rapa (MOG/Rapa) expressed lower levels of a classical DC activation marker CD80, reported as the median fluorescence intensity (MFI) of live (i.e., DAPI$^-$) cells. C) Minimal effect of MPs on the expression of I-A/I-E was observed. All samples were prepared in triplicate and results are representative of three repeat experiments. Error bars on all panels represent mean±SEM.

FIG. 3. Soluble MOG and LPS induced high levels of proliferation in CFSE-labelled transgenic T cells specific for MOG peptide, as visualized by distinct peaks of generations of cell division (A), and higher percent of division (B), as defined by the gating scheme shown in panel A. Particles encapsulating Rapa or MOG and Rapa restrained this proliferation, while Empty MPs and MOG MPs exhibited minimal effects on proliferation. All samples were prepared in triplicate and results are representative of two repeat experiments. Error bars represent mean±SEM.

FIG. 12. Mice treated with Empty MPs (left) exhibit typical LN organization—distinct T and B cell zones and distributed dendritic cells. In contrast, mice treated with MOG/Rapa MPs (right) exhibit an increased frequency of dendritic cells as well as enhanced intermingling of B and T cells.

DESCRIPTION OF THE DISCLOSURE

Figure 1:
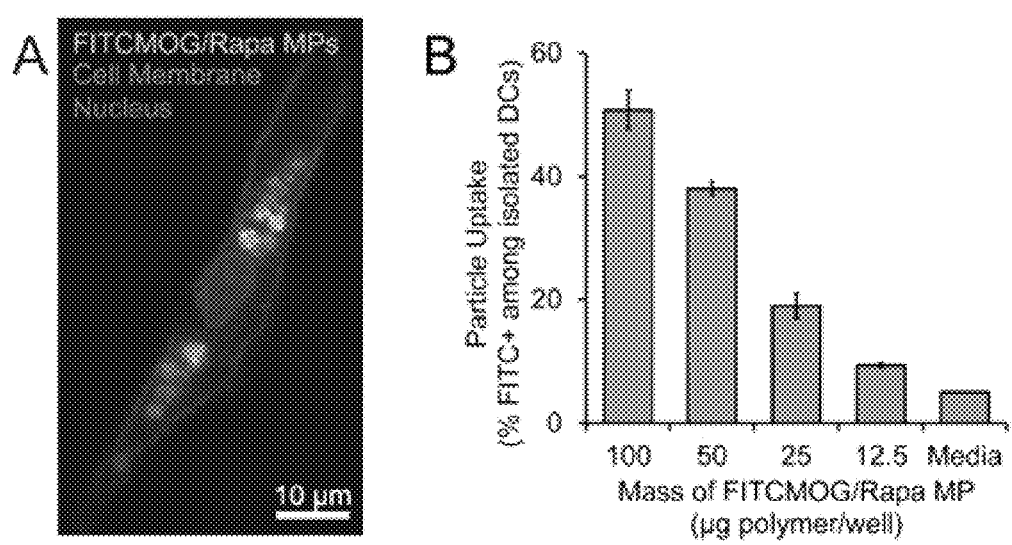
FIG. 1. Microparticles (MPs) encapsulating fluorescent peptide (FITCMOG) and Rapa were incubated with CD11c$^+$ splenic DCs. A) Fluorescence microscopy was used to visualize internalization of MPs. B) Flow cytometry was used to confirm dose-dependent uptake after incubation with serial dilutions of particles. For flow cytometry, MP treated samples were prepared in triplicate and results are representative of two repeat experiments. Error bars represent the mean±SEM.

The present disclosure is broadly related to inducing immune tolerance in individuals who have autoimmune disorders, and is exemplified via compositions and methods that are shown to be surprisingly efficacious in reducing and even reversing symptoms of MS.

In general, the method comprises administering directly into the lymph node of an individual in need a composition comprising a biodegradable polymer and a therapeutically effective amount of at least one antigen that is positively correlated with MS, in combination with an immunomodulatory compound, such that the progression of the severity of MS symptom(s) in the individual are reduced, halted or reversed. In embodiments, the individual has been diagnosed with or is suspected of having MS, and thus can include individuals who have one or a combination of primary-progressive multiple sclerosis (PPMS), relapsing-remitting MS (RRMS), secondary-progressive MS (SPMS), or progressive-relapsing MS (PRMS). In certain embodiments, the individual has been diagnosed with or is suspected of having PPMS. In this regard, and as is known in the art, PPMS is generally characterized by persistent worsening of neurologic function, but without separate relapses or periods of remission. PPMS thus differs from relapsing forms of MS in that the relapsing forms comprise at least two separate locations of damage in the central nervous system (dissemination in space) that occurred at different time points (dissemination in time). The inflammatory events that result in this damage comprise the relapses (sometimes referred to alternatively as attacks or exacerbations). In contrast, PPMS comprises a gradual change in functional abilities over time. Accordingly, because PPMS and relapsing MS are considered distinct disorders (but are not necessarily mutually exclusive in any particular individual) they have different diagnostic criteria. Specifically, PPMS can be diagnosed based on a combination of criteria that comprises a) at least one year of disease progression, which typically includes worsening of neurological function without remission, and b) at least two of: i) a type of lesion in the brain that is recognized by a medical professional skilled in the art of MS diagnosis; ii) two or more lesions of a similar type in the spinal cord; and iii) evidence in the spinal fluid of a oligoclonal band of immunoglobulins, and/or an elevated IgG index, which are both signs of immune system activity in the central nervous system. In certain embodiments of this disclosure, the individual has been diagnosed with or is suspected of having PPMS. In embodiments, PPMS may be the only type of MS that the individual is suspected of having, or has been diagnosed with. In certain embodiments, a method of this disclosure results in a slowing of the progression of symptoms of PPMS, and can even include a reversal of PPMS progression. In connection with this and as known in the art, common symptoms of MS, which can be encompassed by PPMS, include but are not necessarily limited to fatigue, walking difficulties, spasticity, dizziness and vertigo, blurred vision and pain upon eye movement, bladder and bowel dysfunction, numbness or tingling, sexual dysfunction, pain, and cognitive changes, such as complications in the ability to learn and remember information, problem solving and the like. Less common symptoms include but are not necessarily limited to difficulties with speech or swallowing, tremors, seizures and breathing problems. In embodiments, the present disclosure comprises a method of inhibiting the progression of the severity of one or more of these or other MS symptoms in an MS patient, such as a PPMS patient. In embodiments, inhibiting or reducing a symptom means the severity of the symptom is lessened, and/or the rate at which the symptom progresses is slowed, and/or the symptom is prevented from manifesting, and/or the symptom is eliminated. In one embodiment, the instant disclosure includes a demonstration of reducing MS symptoms using a common and well-characterized model of progressive MS, Experimental Autoimmune Encephalomyelitis (EAE). The demonstration establishes that a single intra-lymph nodal dose of a representative myelin antigen (MOG) and a representative immunomodulatory compound (rapamycin) in a representative biodegradable polymer (comprising poly(lactide-co-galactide) (PLGA)), completely prevented the onset of symptoms of paralysis (a clinical score >0 as explained further below) in 50% of treated mice. Treated mice that did develop disease symptoms exhibited delayed disease onset and less severe symptoms when compared to an untreated control group. Thus, for the first time, the present disclosure provides an unexpected therapeutically feasible approach for lessening, stopping, and even reversing progression of MS symptoms in humans suffering from PPMS, as demonstrated using a clinically relevant model of PPMS. In embodiments, this is achieved using only a single intra-lymph node administration. Such results are surprising, and moreover were obtained without using any surface ligands (or ligands elsewhere in the composition) that would specifically target the composition to any immune cell. Furthermore, it is demonstrated that direct intra-lymph node injection promotes systemic, antigen-specific tolerance. Moreover, direct intra-lymph node injection can result in an inhibition of systemic inflammation. Thus, the disclosure includes surprisingly effective, systemic responses that affect PPMS symptoms, and in embodiments can be achieved from only a single, direct intra-lymph node administration.

In general, methods of the disclosure comprise non-surgical approaches for inducing specific immune tolerance to myelin in an individual in need thereof. In one embodiment, a method of this disclosure comprises directly injecting into a lymph node of the individual an effective amount of a cell free composition comprising a myelin antigen, a biodegradable polymer and at least one tolerogenic agent such that tolerance to the myelin antigen in the individual is induced. Without intending to be constrained by any particular theory, it is considered that induction of tolerance to the myelin antigen can be evidenced by a reduction of one or more MS symptoms in the individual subsequent to the administration. Additionally, in certain aspects, the disclosure includes an increase in Tregs in lymph nodes, spleen, CNS, and any combination thereof, and such Tregs can exhibit antigen specificity.

It is expected that any myelin antigen can be used in embodiments of this disclosure, provided the myelin antigen is recognized in whole or in part by a component of the immune system of the individual in need of treatment (prior to the administration). Those skilled in the art will recognize that myelin is synthesized by different cell types, and can vary in composition and structure, but is defined as the material that makes up the so-called sheath of myelinated axons in vertebrates. Myelin in its form in myelinated axons comprises about 40% water; its dry mass is approximately 70-85% lipids and 15-30% proteins. In general, and without intending to be limited by any particular theory, it is considered that any of the lipids or proteins or fragments thereof that are inappropriately recognized by the immune system of an individual in need of treatment can function as a suitable antigen in the compositions and methods of the present disclosure. In embodiments, the myelin antigen comprises a lipid or immunogenic fragment thereof, exemplary lipids including but not necessarily limited to galactocerebroside and sphingomyelin. In embodiments, the myelin antigen comprises a protein or immunogenic fragment thereof, exemplary proteins including but not necessarily limited to myelin basic protein, myelin oligodendrocyte glycoprotein (MOG), and proteolipid protein. Without intending to be constrained by any particular theory, immunogenic fragments are considered to be those that are recognized by the immune system of an individual who has MS. In embodiments, the present disclosure is considered to result in induction of immune tolerance to such antigens. In embodiments, the antigen comprises or consists of myelin, a peptide fragment thereof, or a combination or peptide fragments.

Various embodiments of the disclosure are demonstrated using rapamycin as a non-limiting representative tolerogenic agent. But it is considered that any tolerogenic agent can be included in compositions of this disclosure. In embodiments, the tolerogenic agent comprises any inhibitor of the mammalian target of rapamycin (mTOR), also known as FK506-binding protein 12-rapamycin-associated protein 1 (FRAP1). In embodiments, the mTOR inhibitor is rapamycin, or a rapalog. In embodiments, the mTOR inhibitor comprises Sirolimus, Temsirolimus, Everolimus, Deforolimus, or a second generation mTOR inhibitor generally known to function as an ATP-competitive mTOR kinase inhibitors, and/or mTORC1/mTORC2dual inhibitors. In embodiments, the tolerogenic agent comprises a cytokine or a chemokine or a growth factor or an interferon or a transcription factor, or other small molecule drugs that may include but are not limited to retinoic acid or mycophenolic acid. In embodiments a combination of tolerogenic agents can be used. In certain embodiments, the composition does not comprise one or a combination of IL-10, INF-gamma, INF-lambda, or transforming growth factor beta 1 (TGF-β1).

In certain embodiments, the composition does not comprise any surface ligand that specifically targets the composition to any cell or tissue. In embodiments, the composition does not comprise any surface ligand or surface antibodies or any antibodies that target the composition to immune cells. In embodiments, the composition dose not comprise antibodies, aptamers or binding partners that bind specifically to cell surface ligands/receptors of dendritic cells. In embodiments, compositions of this disclosure do not include PD2, P2, anti-CD 11 antibody, anti-Dec205 antibody, phosphatidyl serine, RGD, or CS1.

Various embodiments of the disclosure are illustrated using poly(lactide-co-galactide) (PLGA) as a representative biodegradable material, but it is expected that any biodegradable material, including but not necessarily limited to biodegrable polymers can be used, provided that the myelin antigen and the tolerogenic agent can be exposed to immune cells in the lymph nodes concurrent with or subsequent to administration. In embodiments, lipid-stabilized micro and nanoparticles can be used. As an alternative to PLGA, the biodegradable material can comprise poly(glycolide) (PGA), poly(L-lactide) (PLA), or poly(beta-amino esters). In embodiments, the biodegradable material may be a hydrogel, an alginate, or a collagen. In an embodiment the biodegradable material can comprise a polyester a polyamide, or polyethylene glycol (PEG). In embodiments, the antigen and/or the tolerogenic agent are encapsulated with the biodegradable material. In embodiments, the antigen and/or the tolerogenic agent are released over a period of time, such as in an extended release formulation where the components are released on the time scale of hours, days, or weeks. Particles may at the nanoscale (e.g., 50-300 nm, inclusive and including all integers and ranges of integers there between) or the microscale (e.g., 2-5 µm, inclusive and including all integers and ranges of integers there between).

Methods for direct intra-lymph node administration are known in the art and improvements thereof as further described herein are encompassed in this disclosure. In certain embodiments, vaccination is achieved using ultrasound guidance to inject the formulation into the lymph node.

In embodiments, the disclosure comprises kits for prophylaxis and/or therapy for MS. The kits can comprise a myelin antigen and a tolerogenic agent in a single formulation, or in separate formulations for mixing together. The kits can comprise a biodegradable material for use in preparing a formulation for direct intra-lymph node administration. The kits can comprise a suitable buffer and pharmaceutically acceptable excipients, carriers and the like. The components can be included in separate containers, or a single container with separate compartments. The containers can include sterile components, vials, ampules, tubes, a bolus, etc. The kits may comprise a needle suitable for direct administration of a composition of this disclosure to one or more lymph nodes, and a syringe, and/or other components for use in lymph node injection. The kits can comprise printed material, such as instructions, and/or an indication that the kit is for use in treating, for example, a PPMS patient.

The following Examples are intended to illustrate but not limit the disclosure.

EXAMPLE 1

This Example demonstrates synthesis of particles encapsulating self-antigen and/or rapamycin. Poly(lactide-co-galactide) (PLGA) particles were synthesized by double-emulsion/solvent evaporation. Four distinct formulations were prepared to conduct studies described here: 1) Empty (i.e., polymer and stabilizer only), 2) MOG, 3) Rapa, and 4) MOG and Rapa co-loaded (MOG/Rapa). The amino acid sequence of MOG is well known in the art. The MOG peptide used in these Examples unless stated otherwise MOG amino acid residues 35-55, also known in the art as $MOG_{35-55}$). Total particle yield was calculated from the dry weight of a known aliquot and laser diffraction was used to confirm the synthesis of microparticles (MPs) with diameters on the order of 2-3 µm (Table 1). Loading levels of MOG were determined via microBCA, a colorimetric assay to detect peptide concentration. Rapa loading was quantified by UV/Vis spectrophotometry, and loading levels of each cargo per mass of particle, as well as encapsulation efficiencies, were calculated. The successful encapsulation of immune signals in PLGA MPs demonstrates our ability to synthesize and characterize the proposed reverse vaccine formulations. Further, the loading of signals was relatively consistent when comparing individual and co-encapsulation formulations, facilitating the delivery of closely matched doses, while minimizing confounding variables like differences in mass of polymer carrier.

TABLE 1

Characterization of poly(lactide-co-galactide) microparticles (MPs) encapsulating the immune signals myelin peptide (MOG) and/or rapamycin (Rapa). Data pooled from three repeat experiments and reported as mean ± SEM.

| | Polymer Core | | MOG Loading | | Rapamycin Loading | |
|---|---|---|---|---|---|---|
| | % Yield | Diameter (µm) | µg MOG/ mg peptide | Encapsulation Efficiency | µg Rapa/ mg peptide | Encapsulation Efficiency |
| Empty MP | 67.9 ± 4.8% | 2.5 ± 0.2 | N/A | N/A | N/A | N/A |
| MOG MP | 67.9 ± 4.8% | 2.6 ± 0.1 | 9.0 ± 0.8 | 49.2 ± 7.3% | N/A | N/A |
| Rapa MP | 74.6 ± 5.6% | 2.4 ± 0.2 | N/A | N/A | 12.7 ± 5.3 | 38.2 ± 5.3% |
| MOG/Rapa MP | 74.6 ± 5.6% | 3.1 ± 0.5 | 7.7 ± 0.3 | 46.3 ± 5.1% | 13.5 ± 3.9 | 40.5 ± 3.9% |

EXAMPLE 2

This Example demonstrates that controlled MP loading modulates primary immune cell activity in vitro. MP formulations were tested in in vitro assays with primary immune cells to screen their tolerogenic potential. To verify that cells could be internalized by antigen presenting cells (e.g., dendritic cells, DCs), CD11 DCs were isolated from the spleens of C57BL/6J mice by magnetic selection. MPs encapsulating fluorescently tagged peptide (FITCMOG) and Rapa were incubated with DCs and were efficiently internalized in a dose-dependent manner (FIG. 1).

We characterized the effects of our MPs on DCs. First, isolated DCs were treated with soluble lipopolysaccharide (LPS), a strong agonist of innate immunity, to trigger the activation of the cells. To investigate the potential of MPs to attenuate LPS-induced activation, equal masses (100 µg of polymer/well) of MPs were added to wells in the four different formulations: 1) Empty, 2) MOG, 3) Rapa, and 4) MOG/Rapa. After 24 hours of incubation, cells were stained for viability and common markers of activation and analyzed by flow cytometry. Minimal impact of MP formulations on cell viability was detected (FIG. 2A). DCs treated with LPS and MPs encapsulating Rapa or MOG/Rapa expressed lower levels of CD80 (FIG. 2B) and CD86 (not shown) compared with cells treated with LPS only, LPS+ Empty MP or LPS+MOG MP. Thus, this Example confirmed the potential of the materials to restrain inflammatory activation. In these studies, minimal impact on I-A/I-E, a marker associated with antigen presentation via MCHII, was observed irrespective of cargo loading (FIG. 2C). This supports the use of these materials for antigen-specific therapy, as antigen presentation in the presence of regulatory signals (e.g., Rapa) may promote the development of antigen-specific $T_{REGS}$.

We investigated the capacity of MPs to restrain the function and development of inflammatory T cells (i.e., proliferation). A co-culture model using cells from a transgenic mouse strain, 2D2, in which the majority of CD4+ T cells express T cell receptors specific for MOG peptide was employed. Briefly, DCs from C57BL/6J mice were prepared as described above and, with the exception of media controls, treated with soluble MOG peptide and LPS to induce high levels of DC activation and, subsequently, 2D2 T cell proliferation upon recognition of their cognate antigen. The four MP formulations were added to investigate whether MPs could restrain proliferation induced by the soluble factors. After 24 hours of DC-MP incubation, CD4+ T cells were isolated from the spleens of 2D2 mice and labeled with a fluorescent dye (carboxyfluorescein succinimidyl ester, CFSE) and added to cultures. This dye serves as a tool to track proliferation; as cells divide, the dye molecules are split between two daughter cells, effectively diluting the dye concentration by a factor of two. As cells continue to proliferate, distinct generations of cell division can be visualized and quantified by flow cytometry.

In these experiments, cells treated with soluble MOG and LPS exhibited high levels of proliferation, as did cells treated with soluble MOG and LPS plus Empty MPs or MOG MPs (FIG. 3). In contrast, MPs encapsulating Rapa suppressed T cell proliferation in the presence of soluble MOG and LPS, as indicated by a lower percentage of cells proliferating beyond Generation 0, using the gating scheme shown. Notably, co-loaded MOG/Rapa MPs were also able to restrain proliferation, despite the inclusion of the specific antigen, MOG. This result indicates that the co-delivery of autoantigen and regulatory signals may be able to restrain inflammatory T cell activity.

EXAMPLE 3

This Example demonstrates that i.LN. delivery of MOG/Rapa MPs prevents or delays autoimmunity in mice.

We investigated whether the tolerogenic effects observed in vitro would translate to control of autoimmunity in vivo after targeted delivery of particles to the inguinal LNs of mice. A common, well-characterized model of progressive MS, Experimental Autoimmune Encephalomyelitis (EAE) was induced according known approaches and the manufacturer's instructions (Hooke Laboratories). Briefly, naïve C57BL/6J mice were immunized with an emulsion of MOG peptide and Complete Freund's Adjuvant, a potent immunostimulatory signal. Together, these signals trigger the expansion of myelin-specific CD4+ cells with inflammatory phenotypes (i.e., $T_H1$ and $T_H17$). Two and twenty-four hours later (two total doses), mice were administered pertussis toxin, which compromises the blood brain barrier, allowing myelin-specific CD4+ cells to infiltrate into the central nervous system (CNS) and attack the myelin sheath. The resultant neurodegeneration presents as progressive paralysis in the mice, which is monitored daily and assigned a clinical score to reflect disease severity (0—no symptoms, 1—limp tail, 2—hind limb weakness, 3—hind limb paralysis, 4—full hind limb and partial front limb paralysis, and 5—moribund).

Figure 4:
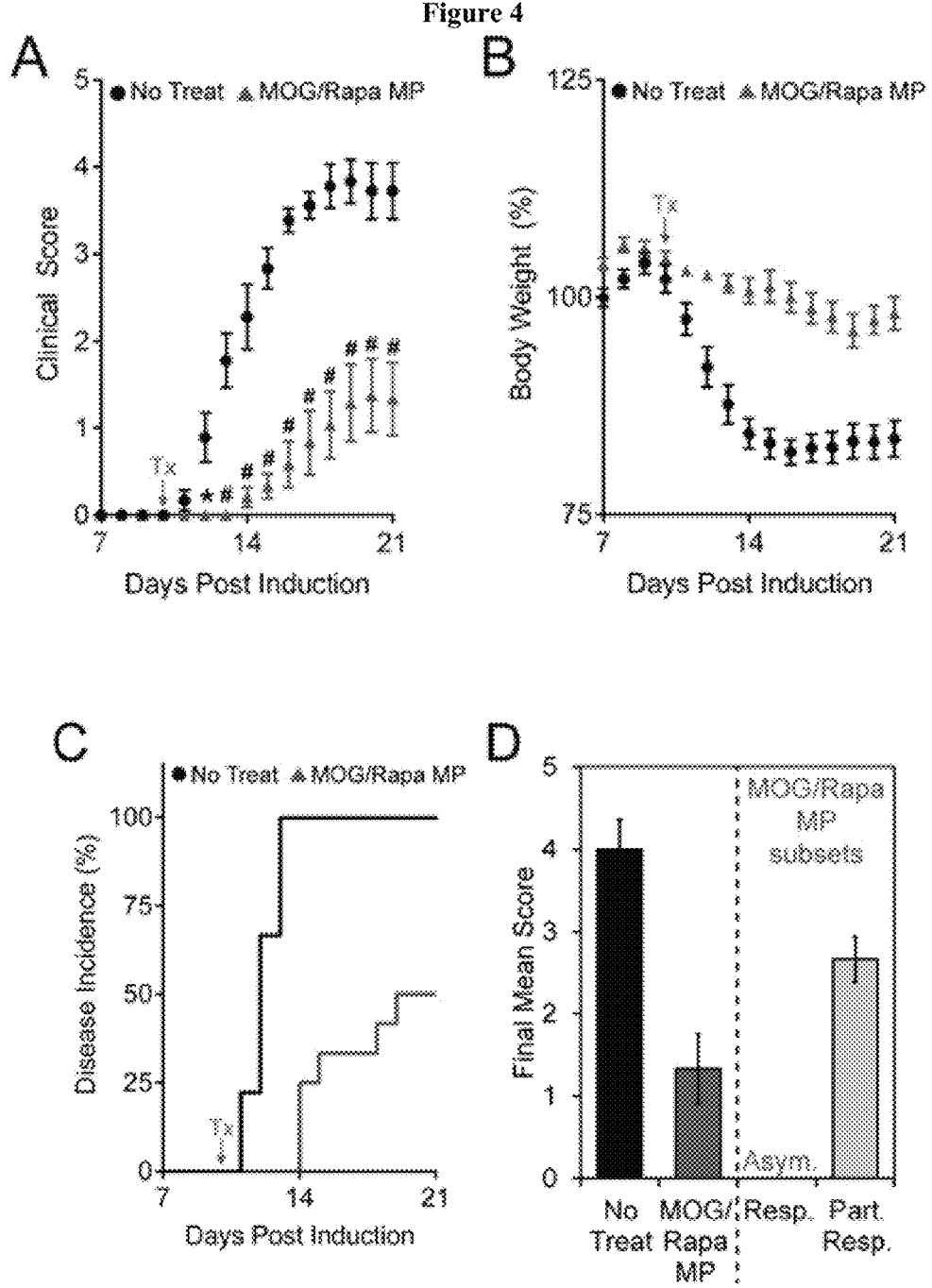
FIG. 4. A) A single, early therapeutic i.LN. treatment (Tx, green arrows) with MOG/Rapa MPs significantly reduced mean clinical disease score (A) and inhibited the weight loss typically associated with EAE (B). C) MOG/Rapa MPs prevented or delayed the onset of clinical symptoms in mice. D) Mice that developed symptoms in the MOG/Rapa MP group, termed "Partial Responders" exhibited less severe disease symptoms compared with induced, but untreated mice, as represented by the mean score at the conclusion of the experiment (Day 21). Data pooled from two similar experiments. Untreated n=9; MOG/Rapa MP n=12. *=p≤0.05, #=p≤0.0001.

For the first study, MPs co-loaded with MOG and Rapa were used. After EAE induction, mice were either left untreated (No Treat) or administered a single dose of MOG/Rapa MPs i.LN. at the approximate onset of disease symptoms (Day 10). Mice receiving MOG/Rapa MPs exhibited significantly lower clinical scores (FIG. 4A) and inhibited weight loss (FIG. 4B) compared to untreated control mice. Strikingly, this single intervention with MOG/Rapa MPs completely prevented the onset of symptoms of paralysis (i.e., clinical score >0) in 50% of mice, termed "Responders." Further, the mice that did develop disease symptoms in the MOG/Rapa group, termed "Partial Responders," exhibited delayed disease onset (FIG. 4C) and less severe symptoms (FIG. 4D) when compared to the untreated control group. These results indicate that local i.LN. delivery of biomaterials is a feasible approach to drive systemic control of autoimmunity, without broad exposure of tissue to strong immune cues, in human progressive MS patients.

EXAMPLE 4

This Example demonstrates that i.LN. injection confers enhanced therapeutic effect over peripheral route. We conducted experiments to test two potential advantages of i.L.N. administration: 1) enhanced potency and efficacy, and 2) minimized off-target effects due to localization of signals in LNs rather than systemic administration. In particular, an experiment was conducted to benchmark i.LN. delivery against a peripheral route commonly used in vaccination, intra-muscular (i.m.) injection. Mice were induced with EAE and treated either i.LN. or i.m. with Empty or MOG/Rapa MPs ten days post induction. The i.m. injections were administered bilaterally in the hind limbs, and incorporated the same dose of MPs as i.LN. injection regimens.

Figure 5:
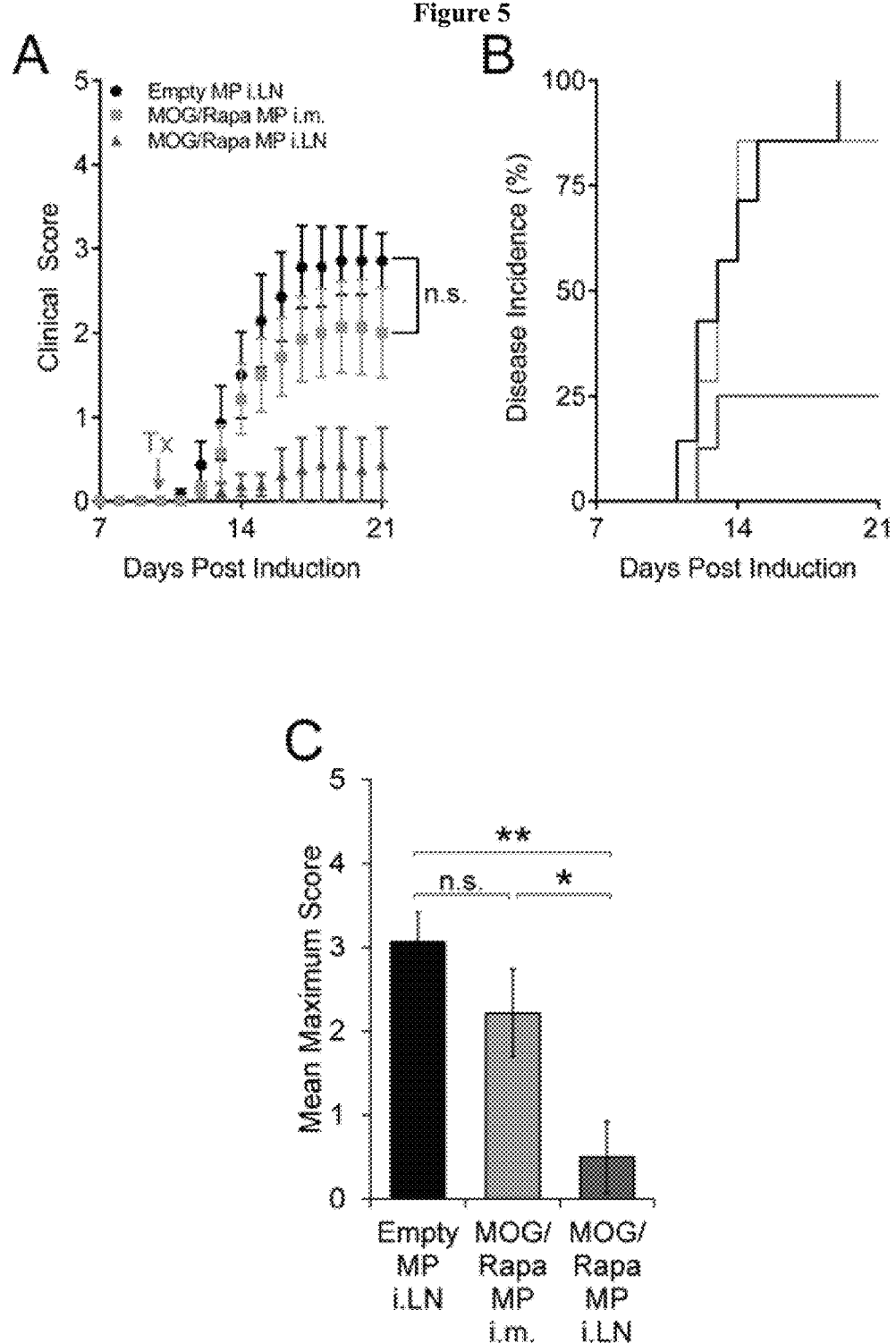
FIG. 5. Intra-lymph node (i.LN.), but not intra-muscular (i.m.), injection of MOG/Rapa MPs significantly reduced symptoms of paralysis, as indicated by lower mean clinical score throughout the study (A), incidence of disease (B) and mean maximum score (C). Empty MP i.LN. n=7; MOG/Rapa MP i.m. n=7; MOG/Rapa MP i.LN. n=8; *=p≤0.05, **=p≤0.01.

No significant differences were observed in clinical score progression of untreated mice and mice administered Empty MPs i.LN. was observed (data not shown). This result confirmed that any tolerogenic effect could be attributed to encapsulated cargo, rather than the carrier or injection procedure. Mice treated i.LN. with MOG/Rapa MPs again exhibited significantly reduced clinical score progression (FIG. 5A), incidence of disease (FIG. 5B) and mean maximum score (FIG. 5C). i.m. injection of MOG/Rapa MPs did not provide any therapeutic benefit compared with Empty MPs. Our results demonstrated a striking therapeutic advantage of targeted LN delivery over a conventional route.

EXAMPLE 5

Figure 6:
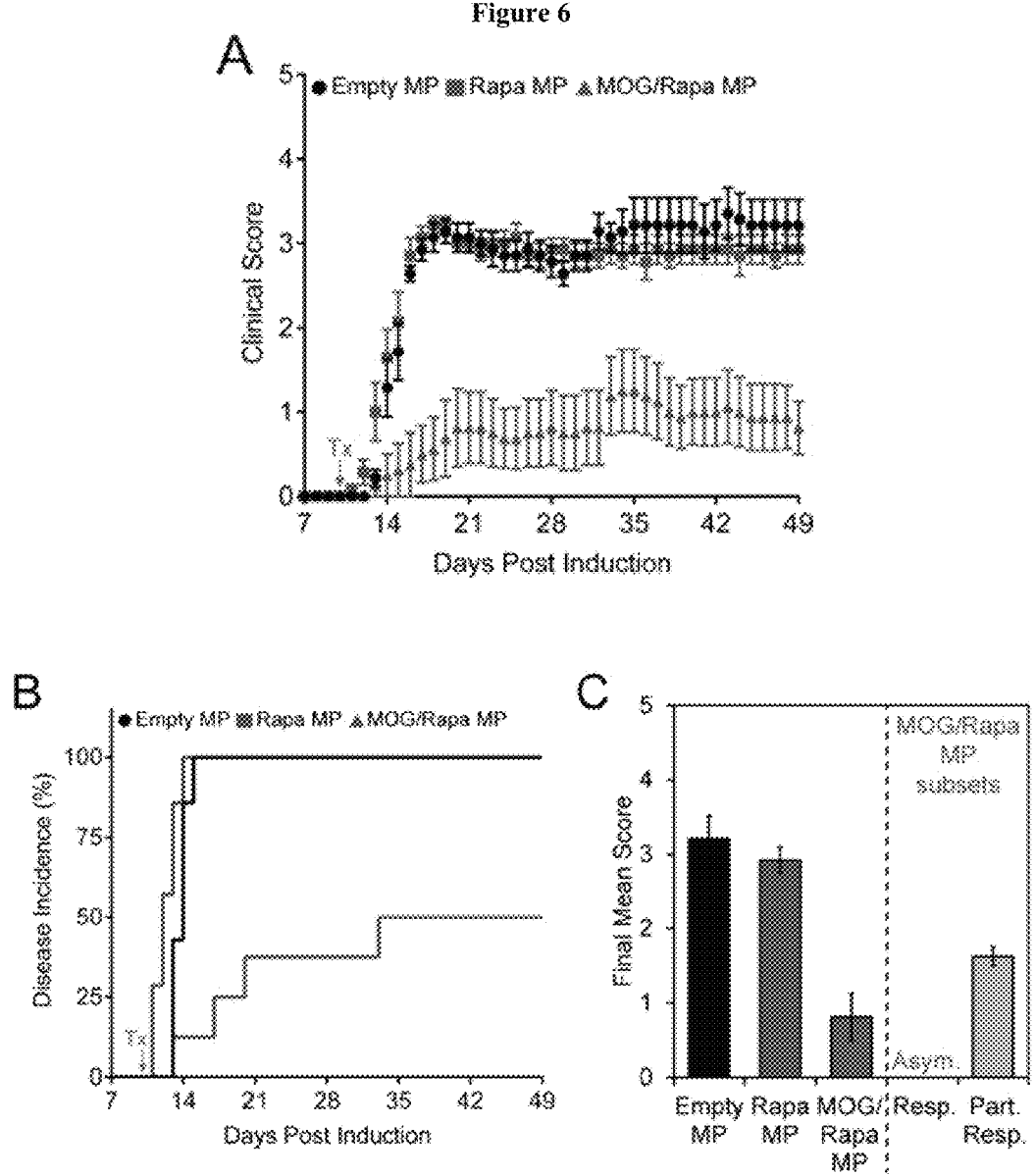
FIG. 6. Early therapeutic i.LN. treatment (Tx, green arrows) with MOG/Rapa MPs significantly reduced mean clinical score (A, C) and disease incidence (B), an effect that was sustained throughout the experiment with only a single dose. In contrast, Rapa MPs exhibited no therapeutic effect on mean score, disease onset and incidence, or final mean score compared with Empty MPs. Empty MP n=7; Rapa MP n=7; MOG/Rapa MP n=8.

This Example demonstrates that the tolerogenic effect is elicited in compositions comprising an autoantigen in an MP formulation. We conducted experiments to determine if the therapeutic effect was due to broad immunosuppression, and accordingly analyzed whether the regulatory cue (i.e., Rapa) alone would confer the same therapeutic benefits. We induced mice with EAE and treated ten days post induction i.LN. with Empty MPs, Rapa MPs or MOG/Rapa MPs. MOG/Rapa MPs exhibited a similar tolerogenic effect to the previous studies. Further, mice were monitored for an additional four weeks (49 days total), and the single treatment ten days post induction was sufficient to maintain significantly reduced clinical score (FIG. 6A, C) and incidence of disease (FIG. 6B) throughout the duration of the experiment.

Notably, Rapa MPs conferred no therapeutic benefit, suggesting that the incorporation of self-antigen into MPs was important to generate a therapeutic effect. This result indicates that i.LN. delivery of materials can be used to polarize myelin-specific immune responses.

EXAMPLE 6

Figure 7:
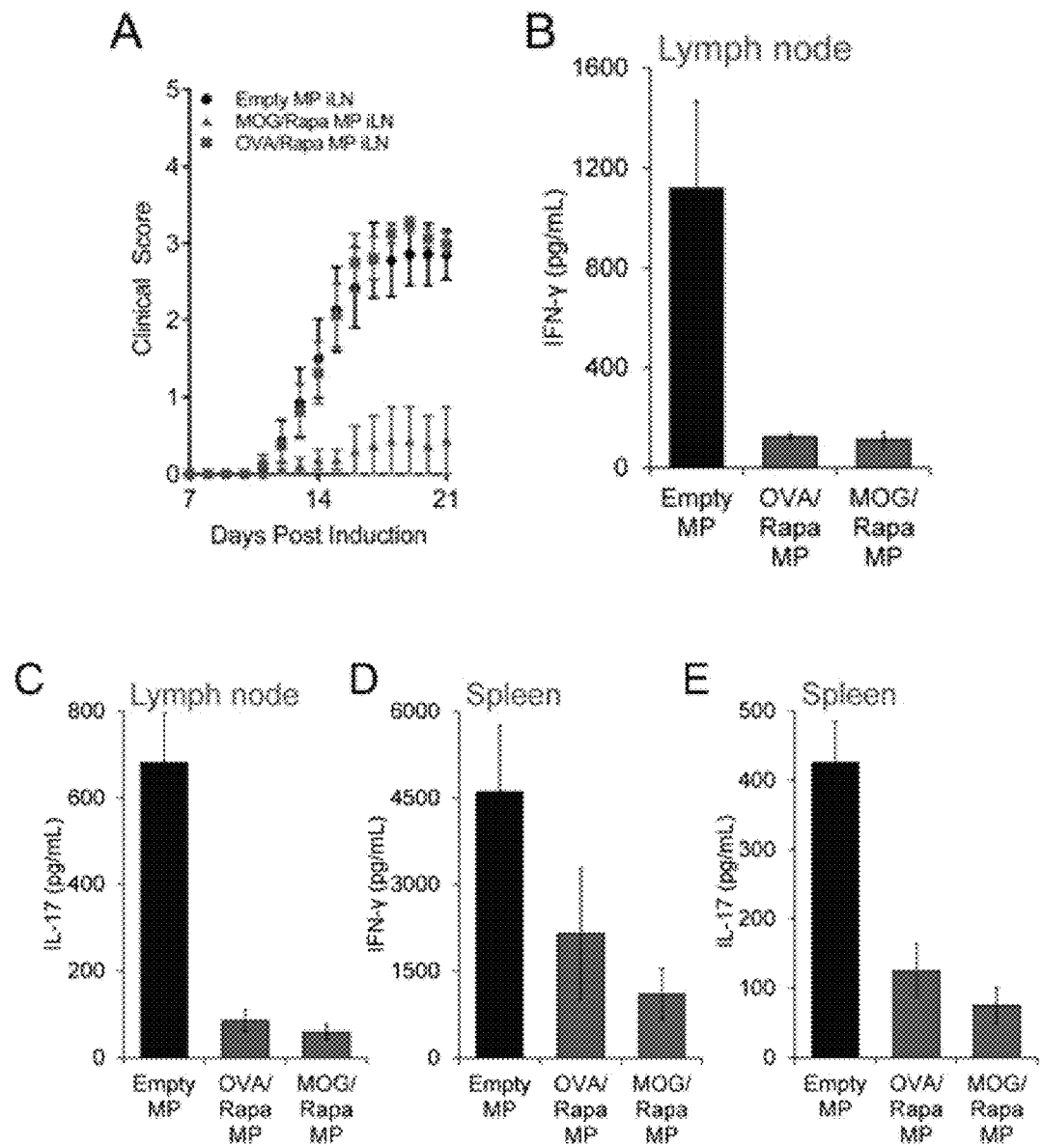
FIG. 7. i.LN. injection of MOG/Rapa MPs restrained disease symptoms of EAE (A), as well as local (B, C) and systemic (D, E) secretion of inflammatory cytokines in response to MOG restimulation. i.LN. injection with OVA/Rapa MPs provided no therapeutic benefit, but strongly suppressed inflammatory cytokine secretion in the treated inguinal LNs and to less of an extent, the spleen. Empty MP n=7; MOG/Rapa MP n=8; OVA/Rapa MP n=8.

This Example demonstrates that MOG/Rapa MPs control local and systemic inflammatory response to autoantigen. To analyze whether embodiments of this disclosure could control inflammatory cellular responses to myelin autoantigen, we conducted an ex vivo restimulation study. Briefly, mice were induced with EAE and treated i.LN. on Day 10 with either Empty MPs, MOG/Rapa MPs or MPs encapsulating Rapa and an irrelevant peptide fragment from the model antigen ovalbumin, $OVA_{323-339}$ (OVA/Rapa MPs). After 21 days, the injected inguinal LNs and spleen were collected from mice in each group. These tissues were processed into single cell suspensions, and a uniform number of cells from each sample was put into culture and restimulated with MOG peptide. After 48 hours, supernatants were collected and Enzyme-linked immunosorbent assay (ELISA) was used to quantify the secretion of inflammatory cytokines IFN-γ and IL-17. Mice treated with Empty MPs developed severe disease-induced paralysis (FIG. 7A) and isolated cells secreted high levels of inflammatory cytokines in both the LN (FIG. 7B, C) and spleen (FIG. 7D, E). In contrast, treatment with MOG/Rapa MPs significantly reduced clinical score and suppressed the autoantigen triggered secretion of inflammatory cytokines. This trend was observed in both the LN and the spleen, indicating that local treatment could control both local and systemic inflammatory responses. Interestingly, OVA/Rapa MPs conferred no therapeutic benefit, but exerted dramatic suppression of inflammatory cytokine secretion in the LN. Further, this suppression was also observed in the spleen, although to less of an extent than in the LN. Together, and without intending to be bound by any particular theory, these results suggest that MPs incorporating Rapa may be generating a local suppressive environment in the injected LN, but that the inclusion of MOG promotes systemic, antigen-specific tolerance.

EXAMPLE 7

This Example demonstrates that i.LN. delivery of MPs drives different cell phenotypes in local and distal tissues. To characterize cellular changes induced by i.LN. delivery of MPs that underpin tolerance, cell phenotypes were analyzed by flow cytometry. Mice were induced with EAE and treated on Day 10 with either Empty or MOG/Rapa MPs i.LN. On Day 12, injected inguinal LNs and spleen were collected, processed and pulsed with MOG as above. Cells were stained or the expression of key transcription factors hallmark of different phenotypes of T cells, Foxp3, RORγ, and Tbet to quantify the frequency of $T_{REG}$, $T_H17$, and $T_H1$ cells, respectively.

Figure 8:
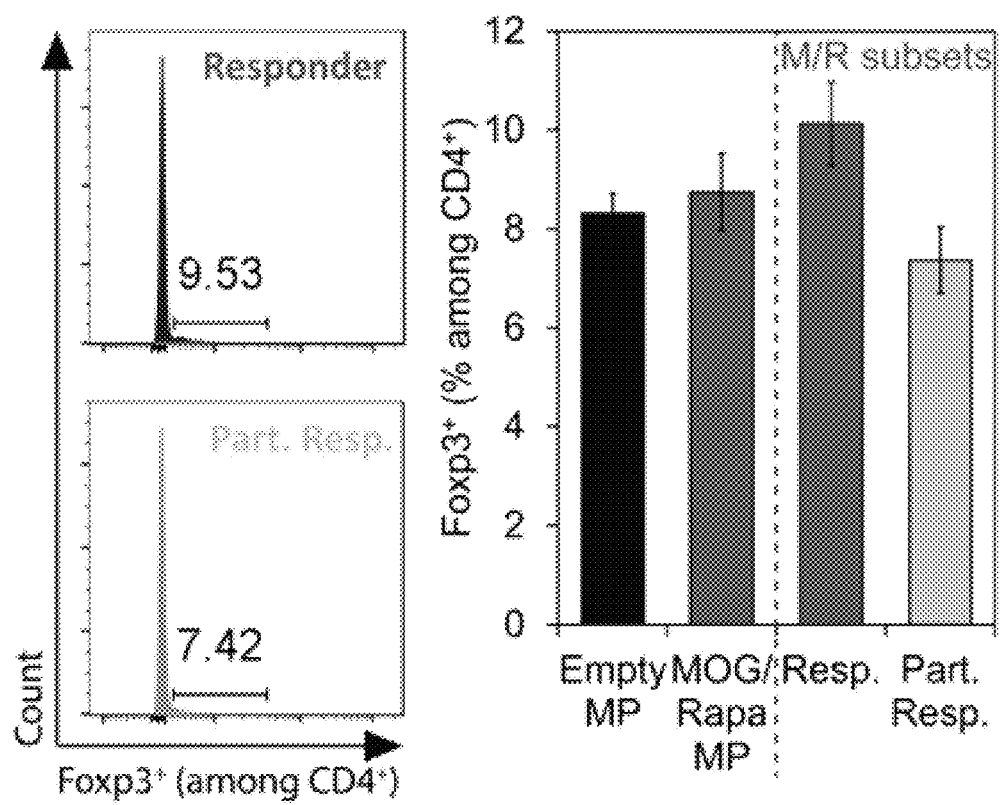
FIG. 8. "Responders," mice that never develop detectable symptoms of disease, express higher levels of regulatory Foxp3 compared with "Partial Responders" in the MOG/Rapa MP treated group.

Interestingly, in the LN, no significant differences across the expression of any of these transcription factors comparing Empty MP treated mice to MOG/Rapa MP treated mice were observed (data not shown). Further analysis of the MOG/Rapa MP group showed that mice that presented with no detectable symptoms of disease "Responders" expressed higher levels of Foxp3 than the "Partial Responders" (FIG. 8).

Figure 9:
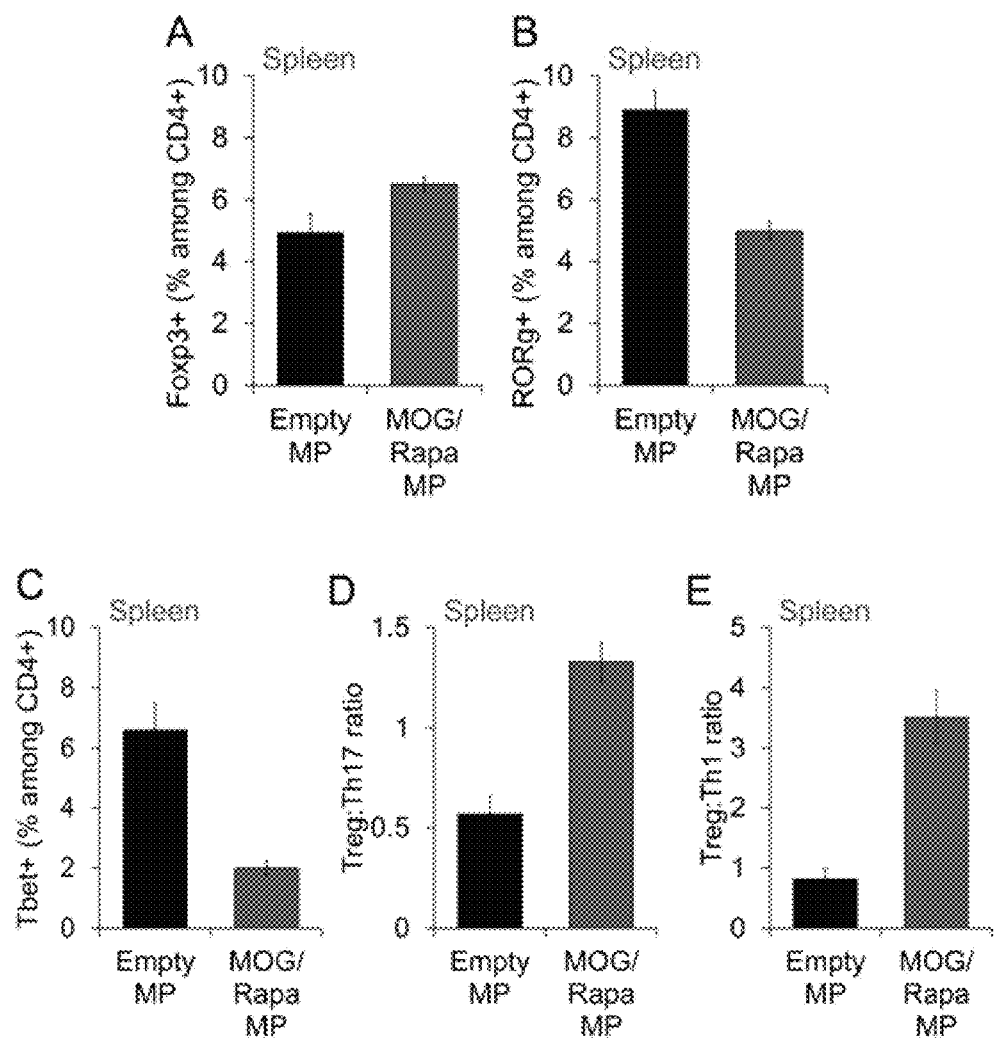
FIG. 9. Cells isolated from the spleens of mice treated i.LN. with MOG/Rapa MPs express higher levels of regulatory transcription factor Foxp3 (A), and lower levels of inflammatory transcription factors RORγ (B) and Tbet (C). Further, Foxp3$^+$ T$_{REG}$ cells outnumbered inflammatory T$_H$17 (D) and T$_H$1 cells (E) calculated as the %Foxp3$^+$/%RORγ$^+$ and %Foxp3$^+$/% Tbet$^+$, respectively.

When we investigated the expression of these same markers in the spleen, we saw an up-regulation of Foxp3 (FIG. 9A) and a down-regulation of both RORγ (FIG. 9B) and Tbet (FIG. 9C). Further, in mice treated with MOG/Rapa MPs, the ratio of regulatory cells to effector cells was increased (FIG. 9D, E), suggesting a skewing of T cell polarization towards regulatory T cell phenotypes. These observed differences at a single time point in two tissues indicate that local treatment with MOG/Rapa MPs may cause local suppressive effects, but generate systemic control of disease via a regulatory T cell mechanism.

EXAMPLE 8

Figure 10:
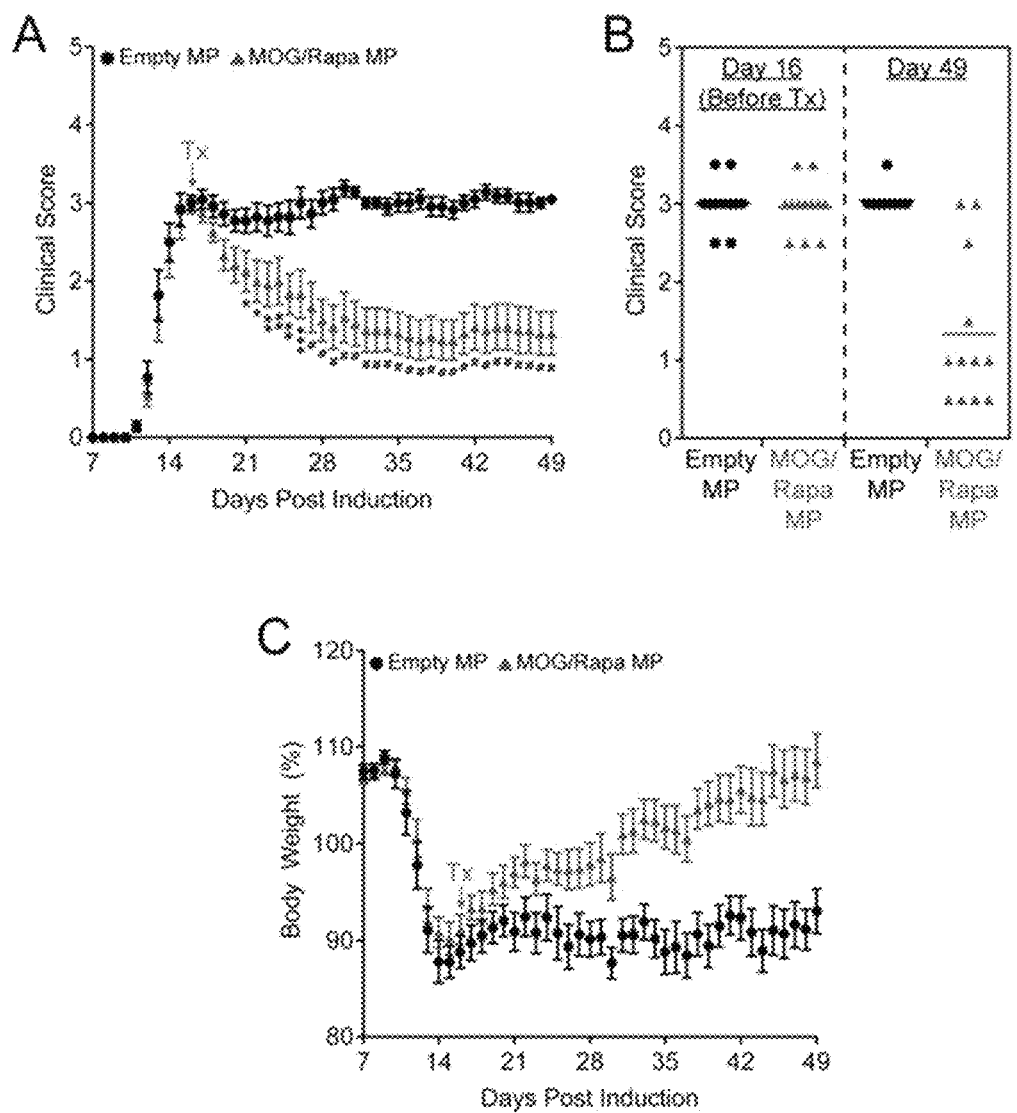
FIG. 10. A single i.LN. treatment with MOG/Rapa MPs at the peak of disease significantly reduced mean clinical score (A), by 1.63 points over the course of the experiment (B) and promoted recovery from EAE-associated weight loss (C). Empty MP n=11; MOG/Rapa MP n=12; *=p≤0.05; =p≤0.01; *p≤0.001; #=p≤0.0001.

This Example demonstrates that MOG/Rapa MPs reverse established disease paralysis. We investigated whether MOG/Rapa MPs could reverse established paralysis. Mice were induced with EAE and on Day 16, the approximate peak of disease, mice were randomized into two groups with equivalent mean scores and injected with either Empty or MOG/Rapa MPs. Mice treated with Empty MPs presented with the same clinical score on the day of treatment (mean 3.0) and the final day of the experiment (mean 3.05), indicating the empty MPs conferred no therapeutic benefit. In contrast, mice treated with MOG/Rapa MPs rapidly decreased in clinical score (FIG. 10A), recovering partial to full hind limb function. Further, the mean score decreased by 1.63 points from the day of treatment to the final day of the experiment (FIG. 10B). Mice also quickly recovered body weight after MOG/Rapa MP treatment (FIG. 10C), another measure of improved overall health and control of disease. Overall, these results support both therapeutic efficacy and mechanism of action in an approach that may reprogram the immune response in established disease.

EXAMPLE 9

Figure 11:
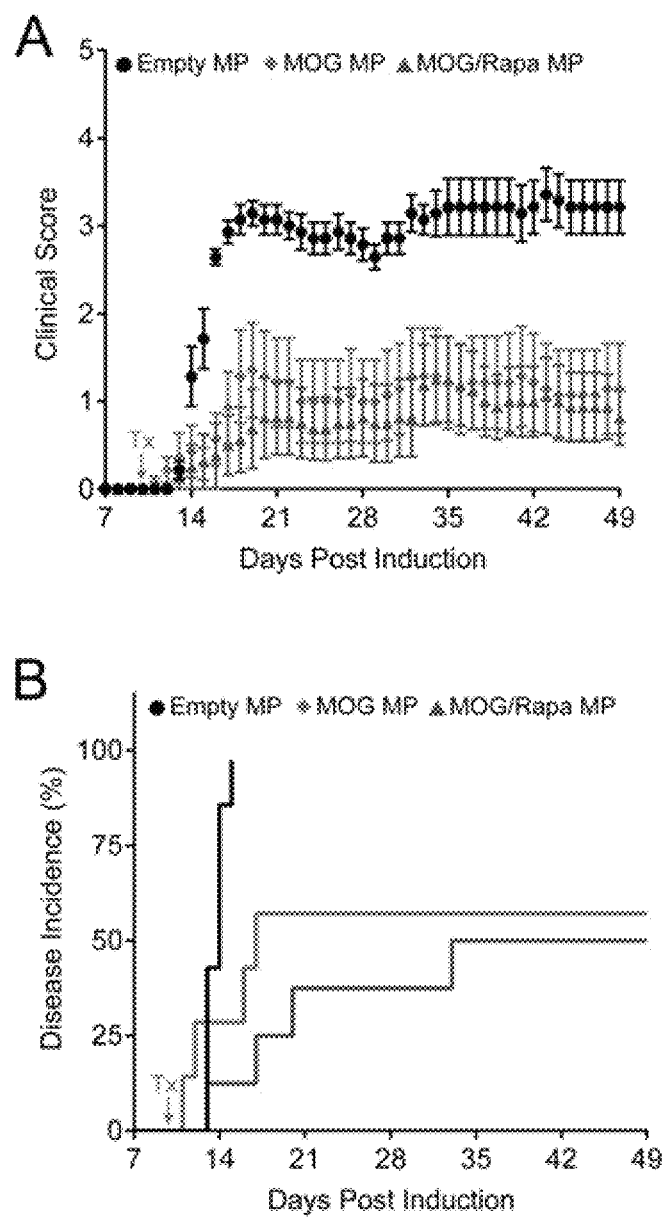
FIG. 11. i.LN injection on Day 10 with MOG/Rapa MPs or MOG MPs attenuates EAE, lowering both mean clinical score (A) and incidence of disease (B) compared with Empty MPs. No significant differences were observed between MOG and MOG/Rapa groups, although a trend of lower clinical score, delayed onset and reduced incidence was observed. Empty MP n=7; MOG MP n=7; MOG/Rapa MP n=8.

This Example demonstrates that i.LN. delivery of biomaterial depots to halt or reverse autoimmunity. Based the foregoing, it is feasible to expect that MOG/Rapa MPs or similar compositions will continue to exhibit significant therapeutic potential in both early and late stage EAE treatment regimens. We conducted a study incorporating treatment with self-antigen only, MOG MPs, and observed a significant decrease in clinical EAE score. Interestingly, treatment with MOG MPs was statistically similar to MOG/Rapa MPs, although there was a trend of reduced clinical score (FIG. 11A), delayed onset and lower incidence of disease (FIG. 11B) when mice were treated with co-loaded MOG/Rapa MPs. It is expected that co-loaded MOG/Rapa MPs will demonstrate an enhanced, synergistic therapeutic effect. This synergistic effect would be reflected in lower clinical scores and reduced incidence of disease.

It is expected that i.LN injection of MOG/Rapa MPs will polarize T cell development towards $T_{REGS}$ and away from $T_H17$ and $T_H1$ phenotypes in a systemic manner. In this regard, as shown in FIG. 12, we obtained images that indicate that we can analyze samples from in vivo studies. For example, the first panel (FIG. 12) highlights changes observed in tolerized (treated with MOG/Rapa MPs) of enhanced frequency of dendritic cells and intermingling of B and T cells after local treatment with immune cues. Further, the second panel demonstrates the potential to stain for a key regulatory marker, Foxp3, after treatement with MOG/Rapa MPs.

Figure 13:
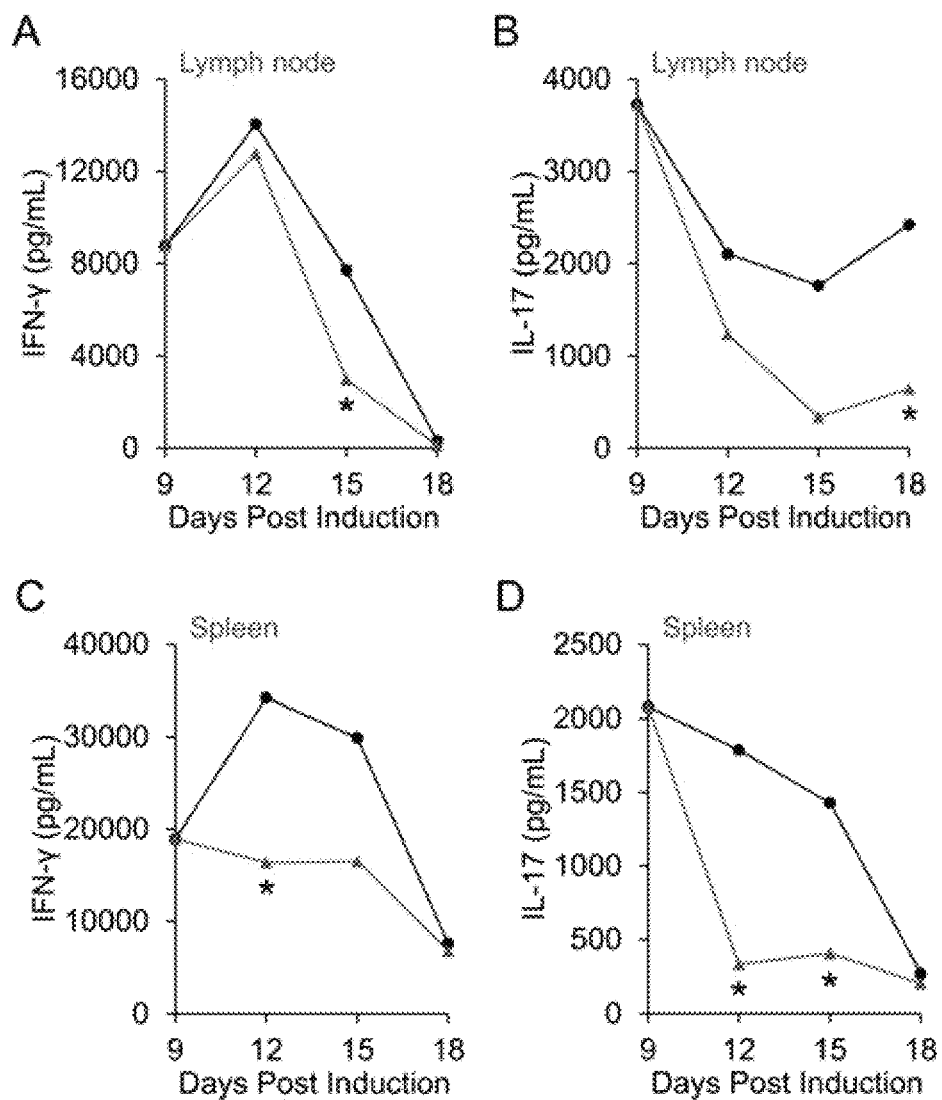
FIG. 13. Cells isolated from the injected inguinal lymph nodes and spleens of mice treated on Day 10 with MOG/Rapa MPs secreted lower levels of inflammatory cytokine after restimulation with autoantigen, MOG. *=p≤0.05.

It is expected that MOG/Rapa MP treatment will result in expression of higher levels of Foxp3. Thus, cells from mice treated with Empty MPs will likely be prompted to secrete inflammatory cytokines and proliferate when they are exposed to MOG, as supported by results described here. In contrast, exposure to an irrelevant antigen peptide should not elicit a response. We conducted a study, characterizing cells from Empty or MOG/Rapa MP treated mice in two tissues, injected inguinal LNs and spleen. We observed that cells from mice treated with MOG/Rapa MPs secreted lower levels of inflammatory cytokine in response to MOG at all time points after i.LN. injection in both tissues (FIG. 13). This result supports the indication that local treatment could restrain systemic inflammation.

EXAMPLE 10

Figure 14:
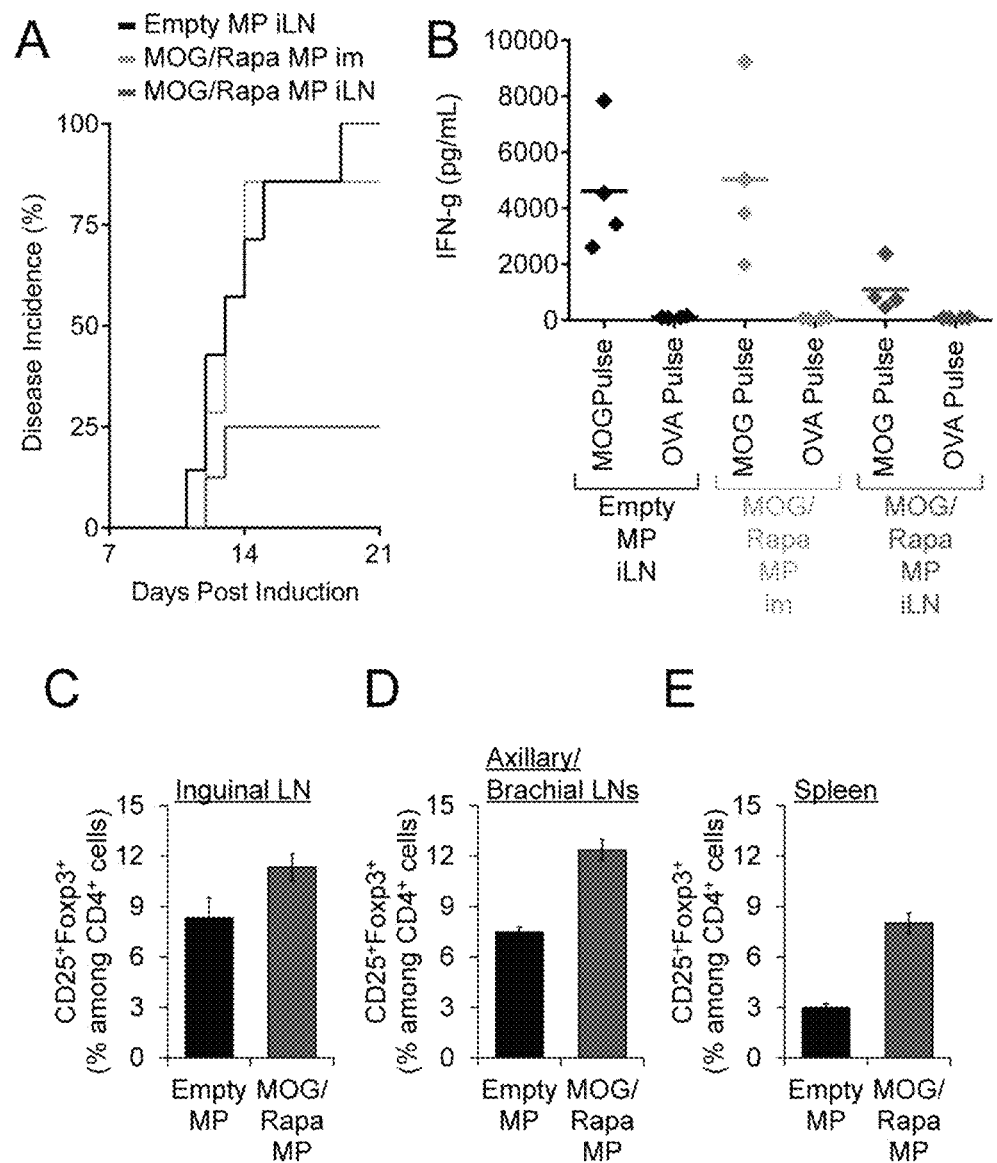
FIG. 14. A) EAE incidence and B) IFN-γ response during restimulation of LNs from mice immunized with empty depots or MOG/rapa depots injected either i.m. or i.LN. TREG levels in the C) inguinal, D) axillary/brachial, and E) spleen.

This Example demonstrates that i.m. injection of MOG/rapa depots does not provide any detectable therapeutic effect, or restrain cytokine secretion when LN- or spleen-resident cells are restimulated with MOG (FIG. 14A, B). We also treated mice inguinal LNs with empty depots or MOG/rapa depots, then assessed TREGS in spleen, and treated and non-treated LNs. This revealed increased TREGS in mice treated with MOG/rapa depots (FIG. 14C-E). These data suggest the local presence of these signals is required for polarizing function, and that tolerance may be driven, at least in part, by TREG expansion and recirculation from the local LN sites.

EXAMPLE 11

Figure 15:
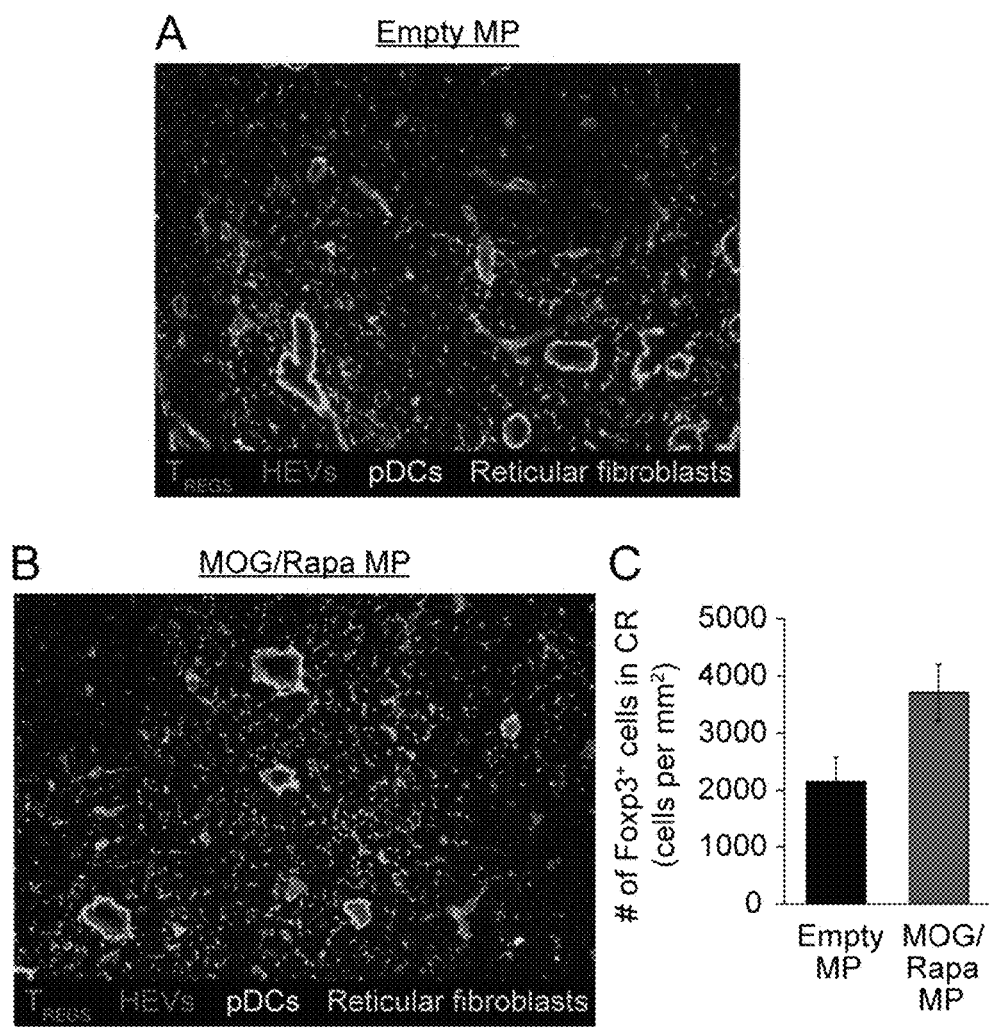
FIG. 15. Histological analysis of TREG infiltration in LNs from EAE mice treated on day 10 with A) empty depots or B) MOG/rapa depots. C) TREG clustering in CR.

This Example demonstrates generation of immune and tolerogenic domains along with co-localization of corresponding T cell populations. We assessed TREGS levels in the cortical ridge (CR) of LNs from mice with EAE. Mice treated with MOG/rapa depots exhibited more TREGS in LNs (FIG. 15A-B), along with increased clustering of these cells in the CR compared with TREGS in mice treated with empty depots (which exhibit no therapeutic effect) (FIG. 15C).

What is claimed is:

1. A method of inducing specific immune tolerance to myelin in an individual in need thereof, the method comprising introducing directly into a lymph node of the individual an effective amount of a composition comprising a myelin antigen, a biodegradable polymer and at least one tolerogenic agent such that tolerance to the myelin antigen in the individual is induced, the composition not comprising any surface ligand that specifically targets the composition to any cell or tissue, wherein the introducing into the lymph node is performed only a single time, and wherein subsequent to the single introducing at least one of the following occurs:
   i) there is a systemic reduction of secretion of inflammatory cytokines in the individual,
   ii) the ratio of T regulatory cells to T effector cells in the spleen of the individual is increased, or
   iii) the amount of IFNγ secreted by lymph node cells and the amount of IFN γ secreted by spleen cells of the individual is lower than a control.

2. The method of claim 1, wherein at least two of i), ii) and iii) occurs.

3. The method of claim 1, wherein all of i), ii) and iii) occur.

4. The method of claim 1, wherein the individual has primary-progressive multiple sclerosis (PPMS).

5. The method of claim 4, wherein at least two of i), ii) and iii) occurs.

6. The method of claim 4, wherein all of i), ii) and iii) occur.

* * * * *